US00PP14542P29

(12) United States Plant Patent
Wijnhout

(10) Patent No.: US PP14,542 P2
(45) Date of Patent: Feb. 17, 2004

(54) HEUCHERA PLANT NAMED 'SWIRLING FANTASY'

(50) Latin Name: *Heuchera sp.*
Varietal Denomination: Swirling Fantasy

(75) Inventor: Aart Wijnhout, Lisserbroek (NL)

(73) Assignee: Witteman + Co., Hillegon (NL)

( * ) Notice: Subject to any disclaimer, the term of this patent is extended or adjusted under 35 U.S.C. 154(b) by 0 days.

(21) Appl. No.: 10/313,118

(22) Filed: Dec. 6, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H Para
(74) *Attorney, Agent, or Firm*—C. A. Whealy

(57) ABSTRACT

A new and distinct cultivar of Heuchera plant named 'Swirling Fantasy', characterized by its uniformly mounded plant habit; grayed purple-colored upper leaf surfaces; dark purple-colored lower leaf surfaces; and pinkish red-colored flowers arranged on upright racemes.

2 Drawing Sheets

Botanical classification/cultivar designation: Heuchera sp. cultivar Swirling Fantasy.

BACKGROUND OF THE INVENTION

The present invention relates to a new and distinct cultivar of Heuchera plant, botanically known as Heuchera sp. and hereinafter referred to by the name 'Swirling Fantasy'.

The new Heuchera is a product of a planned breeding program conducted by the Inventor in Lisserbroek, The Netherlands. The objective of the breeding program is to create new Heuchera cultivars having attractive leaf and flower coloration.

The new Heuchera was discovered by the Inventor in a controlled environment in Lisserbroek, The Netherlands, from seedling progeny from a cross-pollination made by the Inventor of two unidentified Heuchera selections, not patented. The new Heuchera was selected by the Inventor on the basis of its unique leaf and flower coloration.

Asexual reproduction of the new Heuchera by cuttings taken in a controlled environment in Lisserbroek, The Netherlands, since 2000, has shown that the unique features of this new Heuchera are stable and reproduced true to type in successive generations.

SUMMARY OF THE INVENTION

The cultivar Swirling Fantasy has not been observed under all possible environmental conditions. The phenotype may vary somewhat with variations in environment such as temperature and light intensity without, however, any variance in genotype.

The following traits have been repeatedly observed and are determined to be the unique characteristics of 'Swirling Fantasy'. These characteristics in combination distinguish 'Swirling Fantasy' as a new and distinct cultivar of Heuchera:

1. Uniformly mounded plant habit.
2. Grayed purple-colored upper leaf surfaces.
3. Dark purple-colored lower leaf surfaces.
4. Pinkish red-colored flowers arranged on upright racemes.

Compared to plants of the parent selections and other known selections and cultivars of Heuchera, plants of the new Heuchera differ in leaf and flower coloration.

BRIEF DESCRIPTION OF THE PHOTOGRAPHS

The accompanying colored photographs illustrate the overall appearance of the new Heuchera, showing the colors as true as it is reasonably possible to obtain in colored reproductions of this type. Colors in the photographs may differ slightly from the color values cited in the detailed botanical description which accurately describe the colors of the new Heuchera.

The photograph on the first sheet comprises a side perspective view of a typical flowering plant of 'Swirling Fantasy'.

The photograph at the top of the second sheet is a close-up view of a typical flowering raceme of 'Swirling Fantasy'.

The photograph at the bottom of the second sheet is a close-up view of typical leaves of 'Swirling Fantasy'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following description describe plants grown in Boskoop, The Netherlands during the late spring and early summer in an unshaded outdoor nursery and under cultural conditions which approximate commercial practice. During the period of time the photographs and description were taken, day temperatures ranged from 9 to 21° C. and night temperatures ranged from 3 to 11° C. Plants were grown as single plants in two-liter containers and were about two years old when the photographs and description were taken.

Botanical classification: Heuchera sp. cultivar Swirling Fantasy.

Parentage:

*Female, or seed, parent.*—Unidentified Heuchera sp. selection, not patented.

*Male, or pollen, parent.*—Unidentified Heuchera sp. selection, not patented.

Propagation:

*Type.*—By cuttings.

*Time to initiate roots.*—About 20 days at 14° C.

*Time to produce a rooted cutting.*—About 50 days at 20° C.

*Root description.*—Fleshy and well-branched.

Plant description:

*Appearance.*—Perennial; basal rosette plant habit with leaves developing from the base; full, mounded and uniform plant habit with upright racemes with pinkish red-colored flowers. Moderately vigorous growth habit.

*Plant height.*—About 65 cm.

*Plant diameter or spread.*—About 40 cm.

*Foliage description.*—Arrangement: Basal rosette, simple. Length: About 9.5 cm. Width: About 8.4 cm. Shape: Roughly cordate; palmate. Apex: Obtuse, rounded. Base: Cordate. Margin: Crenate. Texture, upper and surfaces: Pubescent. Venation pattern: Palmate, reticulate. Color: Developing leaves, upper surface: Closest to, but slightly more purple than N187B; along midvein, 200A. Developing leaves, lower surface: 187A. Fully expanded leaves, upper surface: Closest to, but more green than N187B; towards the base of the midvein, 147A. Fully expanded leaves, lower surface: 187A. Venation, upper surface: 172A. Venation, lower surface: 187C. Petiole: Length: About 14 cm. Diameter: About 2.5 mm. Texture, upper and lower surfaces: Smooth, glabrous. Color, upper and lower surfaces: 183B.

Flower description:

*Appearance/arrangement.*—Single campanulate flowers arranged on numerous upright racemes; about 72 flowers and flower buds per flowering stem. Flowers face mostly outwardly. Flowering continuous with about eight flowering stems per plant developing throughout the flowering period. Flowers not persistent.

*Fragrance.*—None detected.

*Time of flowering.*—Under natural conditions, plants flower from late April to late June in The Netherlands.

*Flower longevity.*—Flowers last about ten days on the plant.

*Inflorescence height.*—About 26 cm.

*Inflorescence diameter.*—About 8.5 cm.

*Flower size.*—Diameter: About 6 mm. Depth (height): About 7 mm.

*Flower buds.*—Height: About 4 mm. Diameter: About 2 mm. Shape: Elliptic. Color: 51A.

*Sepals.*—Quantity/arrangement: Five sepals; radially symmetrical and fused at base. Length: About 7 mm. Width: About 1.7 mm. Shape: Oblong. Apex: Obtuse. Margin: Entire. Texture: Densely pubescent. Color: When opening, upper surface: 51C. When opening, lower surface: 51A. Fully opened, upper surface: 51B to 51C. Fully opened, lower surface: 51B; towards the base, lighter than 51C.

*Petals.*—Quantity/arrangement: Five minute petals; radially symmetrical. Length: About 3 mm. Width: About 0.9 mm. Shape: Narrowly elliptic. Apex: Acute. Margin: Entire. Texture, upper and lower surfaces: Smooth, glabrous. Color: When opening and fully opened, upper surface: 52B; color becoming closer to 58A with development. When opening and fully opened, lower surface: 52A.

*Penducle.*—Strength: Strong; flexible. Aspect: Upright. Length: About 65 cm. Diameter: About 3 mm. Texture: Densely pubescent. Color: 187A.

*Pedicels.*—Strength: Moderately strong to strong; wiry. Aspect: About 75 to 85° from vertical. Length: About 2.7 cm. Diameter: About 1 mm. Texture: Pubescent. Color: 187A to 187B.

*Reproductive organs.*—Androecium: Stamen number: Five per flower. Anther shape: Orbicular to broadly ovate. Anther length: About 0.5 mm. Anther color: 171A. Amount of pollen: Moderate. Pollen color: 25A. Gynoecium: Pistil number: Two per flower. Pistil length: About 3 mm. Stigma shape: Club-shaped. Stigma color: 155A. Style length: About 2.5 mm. Style color: 155A. Ovary color: 157D.

*Seed/fruit.*—Seeds and/or fruit production has not been observed.

Disease/pest resistance: Resistance to pathogens and pests common to Heuchera has not been observed on plants grown under commercial conditions.

Temperature tolerance: Plants of the new Heuchera have demonstrated good tolerance to night temperatures as low as −12° C. and day temperatures as high as 30° C.

It is claimed:

1. A new and distinct cultivar of Heuchera plant named 'Swirling Fantasy', as illustrated and described.

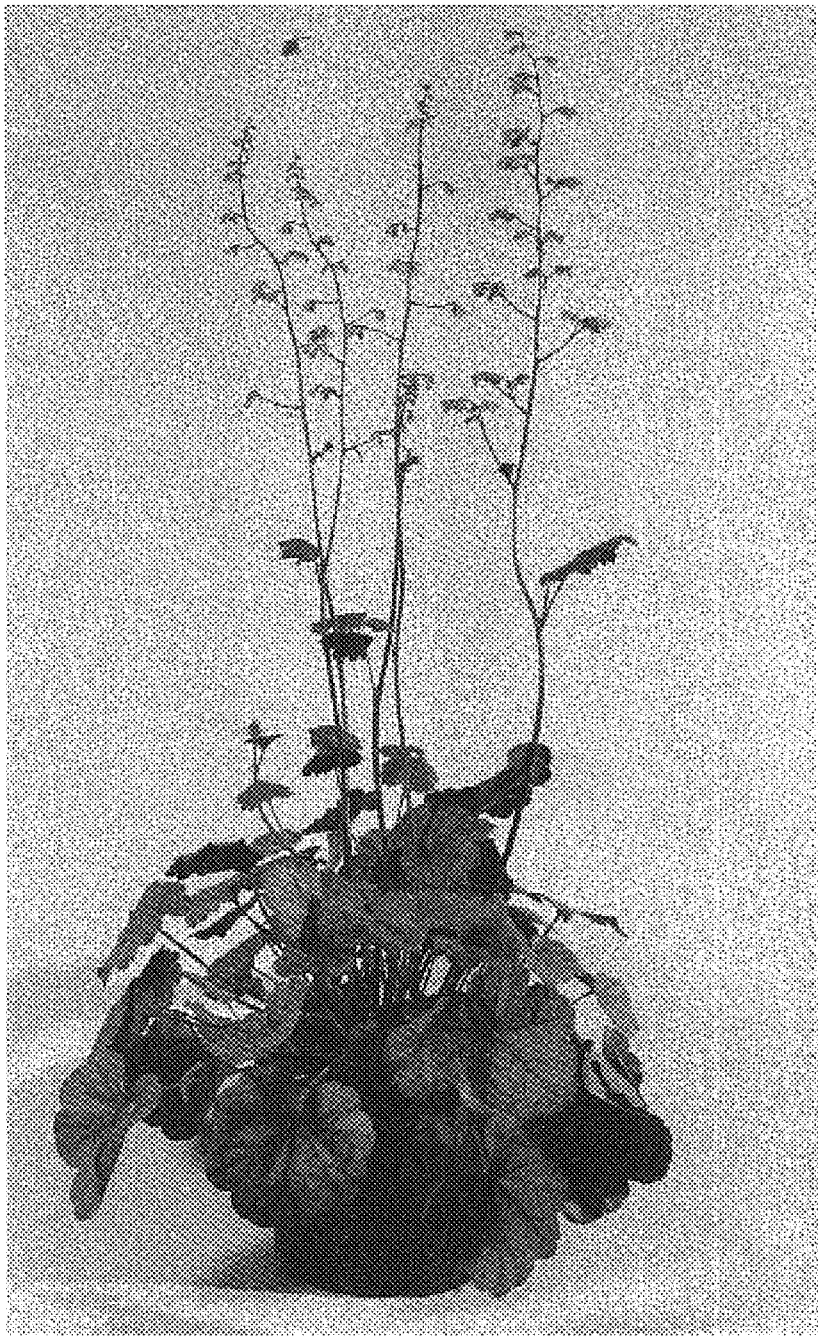

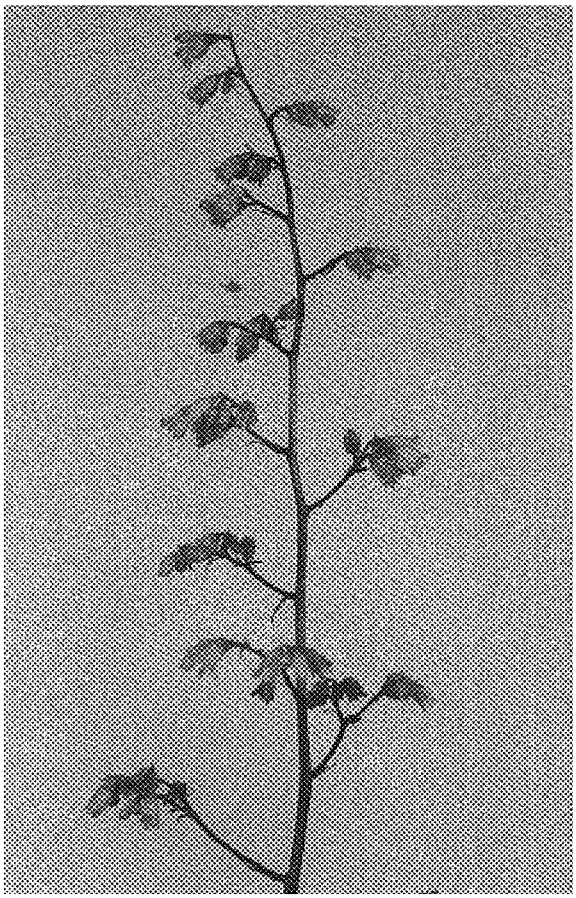
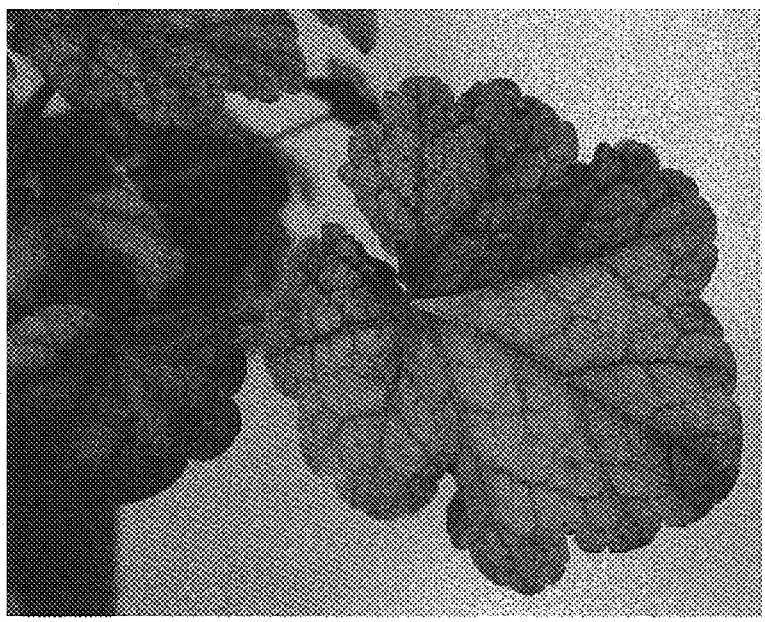

* * * * *